(12) United States Patent
Hartley et al.

(10) Patent No.: US 10,413,434 B2
(45) Date of Patent: Sep. 17, 2019

(54) BRANCH STENT GRAFT DEPLOYMENT AND METHOD

(71) Applicant: Cook Medical Technologies LLC, Bloomington, IN (US)

(72) Inventors: David Ernest Hartley, Wannanup (AU); Michael Lawrence-Brown, City Beach (AU); Wolf Stelter, Bad Soden (DE); Krasnodar Ivancev, Camden (GB); Eric L. G. Verhoeven, AK Glimmen (NL)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/670,782

(22) Filed: Aug. 7, 2017

(65) Prior Publication Data

US 2017/0333235 A1 Nov. 23, 2017

Related U.S. Application Data

(60) Continuation of application No. 13/740,662, filed on Jan. 14, 2013, now Pat. No. 9,724,217, which is a
(Continued)

(51) Int. Cl.
*A61F 2/954* (2013.01)
*A61F 2/07* (2013.01)
(Continued)

(52) U.S. Cl.
CPC .............. *A61F 2/954* (2013.01); *A61F 2/07* (2013.01); *A61F 2/89* (2013.01);
(Continued)

(58) Field of Classification Search
CPC .... A61F 2/954; A61F 2/07; A61F 2/89; A61F 2002/061; A61F 2002/067;
(Continued)

(56) References Cited

U.S. PATENT DOCUMENTS 5,387,235 A 2/1995 Chuter
5,425,765 A 6/1995 Tiefenbrun et al.
(Continued)

FOREIGN PATENT DOCUMENTS

EP 0684022 A2 11/1995
EP 1157674 A2 11/2001
(Continued)

OTHER PUBLICATIONS

Office Action for corresponding Canadian Application No. 2,518,890, dated Oct. 5, 2010, 3 pages.
(Continued)

*Primary Examiner* — Jing Rui Ou
(74) *Attorney, Agent, or Firm* — Brinks Gilson & Lione

(57) ABSTRACT

A deployment device for deploying a self-expanding branched stent graft. The device includes a branched stent graft retained on an introducer. The introducer includes a main catheter and an auxiliary catheter preloaded within the introducer and extending from distal the distal end of the stent graft, into the lumen of the stent graft and through an internal branch in the graft and out of the fenestration.

19 Claims, 15 Drawing Sheets

Related U.S. Application Data continuation of application No. 12/454,797, filed on May 22, 2009, now Pat. No. 8,361,134, which is a division of application No. 10/818,538, filed on Apr. 5, 2004, now Pat. No. 7,537,606.

(60) Provisional application No. 60/510,244, filed on Oct. 10, 2003, provisional application No. 60/460,291, filed on Apr. 3, 2003.

(51) Int. Cl.
*A61F 2/06* (2013.01)
*A61F 2/82* (2013.01)
*A61F 2/95* (2013.01)
*A61F 2/89* (2013.01)

(52) U.S. Cl.
CPC ... *A61F 2002/061* (2013.01); *A61F 2002/067* (2013.01); *A61F 2002/075* (2013.01); *A61F 2002/821* (2013.01); *A61F 2002/9517* (2013.01); *A61F 2220/0075* (2013.01); *A61F 2250/006* (2013.01)

(58) Field of Classification Search
CPC .......... A61F 2002/075; A61F 2002/821; A61F 2002/9517; A61F 2220/0075; A61F 2250/006
See application file for complete search history.

(56) References Cited

U.S. PATENT DOCUMENTS

| | | | |
|---|---|---|---|
| 5,445,646 A | 8/1995 | Euteneuer et al. | |
| 5,617,878 A | 4/1997 | Taheri | |
| 5,628,783 A | 5/1997 | Quiachon et al. | |
| 5,683,449 A | 11/1997 | Marcade | |
| 5,720,776 A | 2/1998 | Chuter et al. | |
| 5,749,920 A | 5/1998 | Quiachon et al. | |
| 5,769,885 A | 6/1998 | Quiachon et al. | |
| 5,968,069 A | 10/1999 | Dusbabek et al. | |
| 5,984,955 A | 11/1999 | Wisselink | |
| 6,015,429 A | 1/2000 | Lau et al. | |
| 6,030,414 A | 2/2000 | Taheri | |
| 6,099,558 A | 8/2000 | White et al. | |
| 6,129,738 A | 10/2000 | Lashinski | |
| 6,136,006 A | 10/2000 | Johnson et al. | |
| 6,156,063 A | 12/2000 | Douglas | |
| 6,206,931 B1 | 3/2001 | Cook et al. | |
| 6,235,051 B1 | 5/2001 | Murphy | |
| 6,280,466 B1 | 8/2001 | Kugler et al. | |
| 6,302,891 B1 | 10/2001 | Nadal | |
| 6,331,188 B1 | 12/2001 | Lau et al. | |
| 6,395,018 B1 | 5/2002 | Castaneda | |
| 6,428,565 B1 | 8/2002 | Wisselink | |
| 6,514,285 B1 | 2/2003 | Pinchasik | |
| 6,524,335 B1 | 2/2003 | Hartley et al. | |
| 6,596,020 B2 | 7/2003 | Vardi et al. | |
| 6,613,072 B2 | 9/2003 | Lau et al. | |
| 6,645,242 B1 | 11/2003 | Quinn | |
| 6,652,567 B1 | 11/2003 | Deaton | |
| 6,682,536 B2 | 1/2004 | Vardi et al. | |
| 6,706,062 B2 | 3/2004 | Vardi et al. | |
| 6,723,116 B2 | 4/2004 | Taheri | |
| 6,770,092 B2 | 8/2004 | Richter | |
| 6,875,229 B2 | 4/2005 | Wilson et al. | |
| 6,939,370 B2 | 9/2005 | Hartley et al. | |
| 7,131,991 B2 | 11/2006 | Zarins et al. | |
| 7,238,198 B2 | 7/2007 | Hartley et al. | |
| 7,435,253 B1 | 10/2008 | Hartley et al. | |
| 8,545,549 B2 | 10/2013 | Hartley et al. | |
| 2001/0016767 A1 | 8/2001 | Wilson | |
| 2001/0037142 A1 | 11/2001 | Stelter et al. | |
| 2002/0040236 A1 | 4/2002 | Lau et al. | |
| 2002/0072790 A1 | 6/2002 | McGuckin et al. | |
| 2002/0091439 A1 | 7/2002 | Baker et al. | |
| 2002/0138088 A1 | 9/2002 | Nash et al. | |
| 2002/0143383 A1* | 10/2002 | Parodi | A61F 2/954 623/1.11 |
| 2002/0156523 A1 | 10/2002 | Lau et al. | |
| 2002/0169497 A1* | 11/2002 | Wholey | A61F 2/07 623/1.13 |
| 2002/0183763 A1 | 12/2002 | Callol et al. | |
| 2002/0198585 A1 | 12/2002 | Wisselink | |
| 2003/0069561 A1 | 4/2003 | Choi | |
| 2003/0114911 A1 | 6/2003 | Lupton | |
| 2003/0120332 A1 | 6/2003 | Hartley | |
| 2003/0135257 A1 | 7/2003 | Taheri | |
| 2003/0199967 A1 | 10/2003 | Hartley et al. | |
| 2003/0204242 A1 | 10/2003 | Zarins et al. | |
| 2003/0208260 A1 | 11/2003 | Lau et al. | |
| 2003/0225446 A1* | 12/2003 | Hartley | A61F 2/95 623/1.11 |
| 2004/0082990 A1 | 4/2004 | Hartley | |
| 2004/0111146 A1 | 6/2004 | McCullagh et al. | |

FOREIGN PATENT DOCUMENTS

| | | |
|---|---|---|
| WO | WO 97/09007 A1 | 3/1997 |
| WO | WO 97/45073 A1 | 12/1997 |
| WO | WO 98/19628 | 5/1998 |
| WO | WO 98/53761 | 12/1998 |
| WO | WO 99/13808 A1 | 3/1999 |
| WO | WO 99/36002 A1 | 7/1999 |
| WO | WO 01/67993 A2 | 9/2001 |
| WO | WO 02/076346 A1 | 10/2002 |
| WO | WO 03/034948 A1 | 5/2003 |
| WO | WO 03/053287 A1 | 7/2003 |
| WO | WO 03/082153 A2 | 10/2003 |
| WO | WO 2004/002365 A1 | 1/2004 |
| WO | WO 2004/017867 A1 | 3/2004 |
| WO | WO 2004/017868 A1 | 3/2004 |

OTHER PUBLICATIONS

Notice of Allowance for corresponding Canadian Application No. 2,518,890, dated Aug. 22, 2011, 1 page.
European Search Report for corresponding EP 09156931 dated Apr. 28, 2009, 3 pages.
Examination Report for corresponding EP 04749755.7 dated Sep. 24, 2007, 3 pages.
Examination Report for corresponding EP 04749755.7 dated Jul. 14, 2009, 3 pages.
Office Action and English translation for corresponding Japanese Application No. 2006-509707, dated Nov. 6, 2009, 5 pages.
International Search Report and Written Opinion for PCT/US2004/010445, dated Oct. 5, 2004, 12 pages.
International Preliminary Report on Patentability for PCT/US2004/010445, dated Oct. 14, 2005, 8 pages.
Jae Hyung Park, et al., Fenestrated Stent-Grafts for Preserving Visceral Arterial Branches in the Treatment of Abdominal Aortic Aneurysms: Preliminary Experience, Journal of Vascular and Interventional Radiology, University College of Medicine, Seoul, Korea, p. 819 (1996) (5 pages).
Non-Final Office Action for U.S. Appl. No. 10/818,538 dated Sep. 19, 2007 (15 pages).
Final Office Action for U.S. Appl. No. 10/818,538 dated Jan. 17, 2008 (12 pages).
Non-Final Office Action for U.S. Appl. No. 10/818,538 dated Jun. 5, 2008 (9 pages).
Final Office Action for U.S. Appl. No. 10/818,538 dated Nov. 25, 2008 (9 pages).
Notice of Allowance for U.S. Appl. No. 10/818,538 dated Mar. 6, 2009 (6 pages).
Non-Final Office Action for U.S. Appl. No. 12/454,797 dated Jul. 20, 2011 (11 pages).
Final Office Action for U.S. Appl. No. 12/454,797 dated Jan. 31, 2012 (15 pages).
Notice of Allowance for U.S. Appl. No. 12/454,797 dated Sep. 19, 2012 (8 pages).

(56) References Cited

OTHER PUBLICATIONS

Non-Final Office Action for U.S. Appl. No. 13/740,662 dated Jan. 15, 2014 (16 pages).
Final Office Action for U.S. Appl. No. 13/740,662 dated May 14, 2014 (17 pages).
Non-Final Office Action for U.S. Appl. No. 13/740,662 dated Dec. 1, 2015 (17 pages).
Final Office Action for U.S. Appl. No. 13/740,662 dated Sep. 7, 2016 (13 pages).
Notice of Allowance for U.S. Appl. No. 13/740,662 dated Apr. 6, 2017(13 pages).

\* cited by examiner

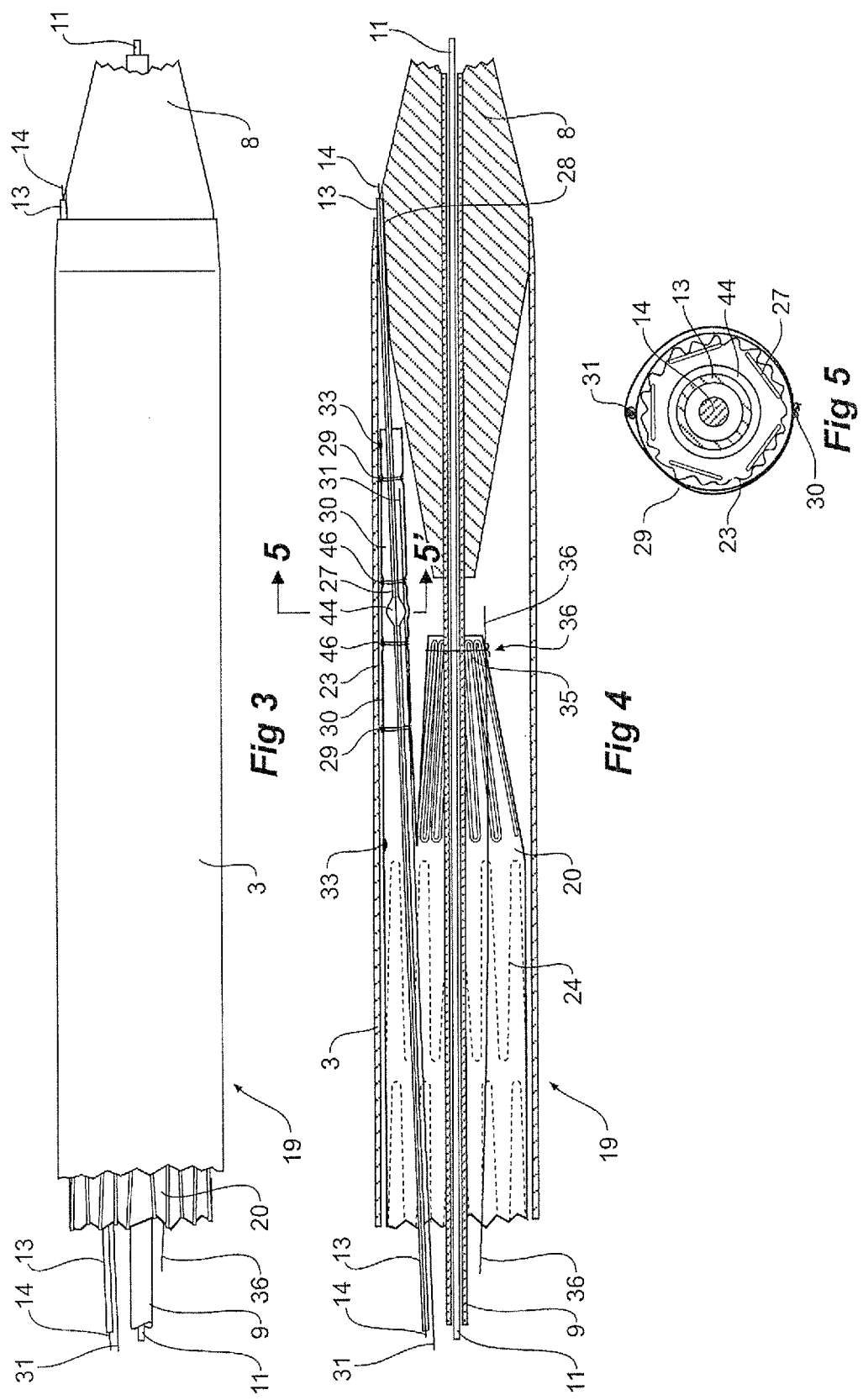

BRANCH STENT GRAFT DEPLOYMENT AND METHOD

RELATED APPLICATIONS

This application is a continuation of U.S. application Ser. No. 13/740,662, filed Jan. 14, 2013, now U.S. Pat. No. 9,724,217, which is a continuation application of U.S. application Ser. No. 12/454,797 filed May 22, 2009, now U.S. Pat. No. 8,361,134, which is a divisional application of U.S. application Ser. No. 10/818,538, filed Apr. 5, 2004, now U.S. Pat. No. 7,537,606 which application in turn claims priority to provisional application Ser. No. 60/510,244, filed Oct. 10, 2003 and Ser. No. 60/460,291, filed Apr. 3, 2003, which are incorporated herein in their entirety.

BACKGROUND

1. Technical Field Text

This Invention Relates to an Endoluminal Deployment System, a Stent Graft for endoluminal deployment and a method of endoluminal deployment of such a stent graft into a vessel with a side branch such as the thoracic arch of a patient.

2. Background Information

The invention is particularly directed towards deploying a stent graft with a fenestration from which or into which a side arm can be deployed to enter one of the arteries that extends from the thoracic arch. These arteries are the innominate artery, the left carotid artery and the left subclavian artery. The invention will generally be discussed in relation to an endoluminal deployment system to enable branch grafting into the left subclavian artery but the invention may equally apply to the other arteries or to other vessels in the human or animal body.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

BRIEF SUMMARY

In one form therefore the invention is said to reside in a deployment system for a stent graft to be deployed into an internal lumen of a patient, the deployment system comprising an introducer with the stent graft retained thereon, the introducer having a proximal end intended to be deployed within a patient in use and a distal end intended to remain outside the patient and an auxiliary guide wire, the auxiliary guide wire extending to adjacent the proximal end of the introducer whereby the auxiliary guide wire can be extended from the proximal end of the introducer so that it can be snared from a side artery to assist with deployment of a stent graft into the side artery.

Preferably the introducer includes a sheath to retain the stent graft in a retracted state on the introducer.

The stent graft may be of a type which includes a side branch and the auxiliary guide wire extends through the side branch. Alternatively the stent graft can include a fenestration and the auxiliary guide wire extends through the fenestration. Alternatively the fenestration can include a graft tube extending into the stent graft from the fenestration either distally or proximally.

The auxiliary guide wire can be retained in an auxiliary catheter extending to the distal end of the introducer and the auxiliary guide wire can extend out between a nose cone on the proximal end of the introducer and a sheath on the introducer.

There may be provided a retention arrangement for the stent graft on the introducer which is adapted to retain the proximal and distal ends of the stent graft onto the introducer and includes trigger wires and trigger wire release mechanisms to release the proximal and distal retention arrangements.

Diameter reducing ties with an associated trigger wire and trigger wire release mechanisms can be used for the side arm stent graft, the diameter reducing ties being used to hold the diameter of the side arm reduced against the force of self expanding stents in the side arm so that it can be drawn into the side branch artery without unduly engaging the walls of the artery.

In a further form deployment device for deploying a branched stent graft in a thoracic arch of a patient, the stent graft being of a type having a main tubular body with a main lumen therethrough and a side arm with a side arm lumen extending therethrough, the deployment device including a main guide wire catheter extending from a proximal end to a distal end, a nose cone at the proximal end of the guide wire catheter an auxiliary guide wire catheter with an auxiliary guide wire extending therethrough extending from the distal end to the nose cone, the stent graft being retained on the main guide wire catheter distally of the nose cone with the main guide wire passing through the main lumen and the auxiliary guide wire extending through the main lumen and the side arm lumen and extending to the nose cone and the side branch being retained on the auxiliary guide wire catheter and a sheath coaxial with the main guide wire catheter and extending to the nose cone and enclosing the stent graft.

Preferably the stent graft and side arm on the stent graft include self-expanding stents and a tubular biocompatible graft.

In a further form the invention is said to reside in a deployment device for deploying a fenestrated stent graft in a thoracic arch of a patient, the stent graft being of a type having a main tubular body with a main lumen therethrough and a fenestration in the tubular body, the deployment device including a main guide wire catheter extending from a proximal end to a distal end, a nose cone at the proximal end of the guide wire catheter, an auxiliary catheter with an auxiliary guide wire extending therethrough extending from the distal end to the nose cone, the stent graft being retained on the main guide wire catheter distally of the nose cone with the main guide wire passing through the main lumen and the auxiliary catheter extending through the main lumen and the fenestration and further extending to the nose cone and a sheath coaxial with the main guide wire catheter and extending to the nose cone and enclosing the stent graft.

Preferably the stent graft is retained on the main guide wire catheter with the side arm extending proximally from its connection point with the main tubular body. Hence when advancing the side arm into the side branch artery the introducer with the stent graft retained on it is advanced proximally to allow the side arm to enter the side branch artery.

The stent graft and side arm on the stent graft may include self-expanding stents and a tubular biocompatible graft material covering the stents. The proximal stent may include barbs. There may also be provided at the distal end of the stent graft a distally extending uncovered self expanding stent with barbs to retain the distal end of the stent graft in the aorta. Alternatively the stent graft may be a proximal portion of a composite stent graft and the distal end of the stent graft can be adapted to be connected to or into another stent graft.

The stent graft may have a diameter of from 30 to 40 mm and a length of from 100 to 200 mm. The side arm may have a diameter of 10 to 15 mm and a length of from 20 to 50 mm. The self expanding stents in the main body of the graft and in the side arm may be Gianturco self expanding zigzag Z stents made from, for example, nitinol or stainless steel.

The deployment device may include a Y branch on the distal end thereof with the auxiliary guide wire catheter extending out of the Y branch. There can be provided a locking arrangement to fix the auxiliary guide wire with respect to the auxiliary guide wire catheter. Alternatively the auxiliary catheter can extend from the distal end of the handle.

In a further form the invention is said to reside in a method of introducing a fenestrated stent graft into the thoracic arch of a patient such that a stent graft can be deployed into the fenestration from the branch artery in the thoracic arch, the method including the steps of; (a) introducing an introducer via a femoral artery so that the fenestration is adjacent the branch artery to be grafted, (b) extending an auxiliary guide wire from the introducer, (c) snaring the auxiliary guide wire from the branch artery by means of a snare catheter introduced via a brachial artery and drawing the auxiliary guide wire into the brachial artery, (d) withdrawing the sheath from the introducer, (e) advancing a side arm stent graft on a side arm introducer over the auxiliary guide wire into the fenestration, (f) releasing the distal and proximal ends of the stent graft, and (g) releasing the side arm stent graft from the side arm introducer. In a further form the invention is said to reside in a method of introducing a branched stent graft into the thoracic arch of a patient such that the branch of the stent graft is deployed into the branch artery in the thoracic arch, the method including the steps of; (a) introducing an introducer via a femoral artery to adjacent the branch artery to be grafted, (b) extending an auxiliary guide wire from the introducer, (c) snaring the auxiliary guide wire from the branch artery by means of a snare catheter introduced via a brachial artery and drawing the auxiliary guide wire into the brachial artery, (d) inserting an artery wall protecting sleeve or catheter over the auxiliary guide wire via the brachial artery and clamping it to the auxiliary guide wire, (e) withdrawing the sheath from the introducer, (f) advancing the introducer proximally and drawing the side arm into the side branch artery using the artery wall protecting sleeve or catheter and the auxiliary guide wire, (g) releasing the distal and proximal ends of the stent graft, (h) releasing the diameter reducing ties on the side arm in the side branch artery, and (i) removing the introducer.

If necessary and depending upon the size of the aneurysm in the thoracic arch after deployment of the stent graft an extension stent graft may be deployed intra-luminally via the branch artery to connect into the side arm.

In the case of grafting into the left subclavian artery the branch artery into which the snare catheter can be introduced is the brachial artery in the left arm.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated by reference in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated by reference in its entirety into this specification.

PCT Patent Publication Number WO98/53761 entitled "A Prosthesis and a Method and Means of Deploying a Prosthesis" discloses an introducer for a prosthesis which retains the prosthesis so that each end can be moved independently. These features and other features disclosed in PCT Patent Publication Number No. WO98/53761 could be used with the present invention and the disclosure of PCT Patent Publication Number No. WO98/53761 is herewith incorporated by reference in its entirety into this specification.

PCT Patent Publication No. WO 03/034948 entitled "Prosthesis For Curved Lumens" discloses prostheses with arrangements for bending the prosthesis for placement into curved lumens. This feature and other features disclosed in PCT Patent Publication No. WO 03/034948 could be used with the present invention and the disclosure of PCT Patent Publication No. WO 03/034948 is herewith incorporated by reference in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated by reference in its entirety into this specification.

Australian Provisional Patent Application N PS3215 entitled "A Stent-Graft Fastening Arrangement", and U.S. patent application Ser. No. 10/602,930, filed Jun. 24, 2003 entitled "Stent-Graft Fastening", and PCT Patent Publication Number WO 2004/002365 disclose arrangements for fastening stents onto grafts particularly for exposed stents. This feature and other features disclosed in Australian Provisional Patent Application Number No. PS3215 and U.S. patent application Ser. No. 10/602,930, filed Jun. 24, 2003, and PCT Patent Publication Number WO 2004/002365 could be used with the present invention and the disclosure of Australian Provisional Patent Application Number PS3215 and U.S. patent application Ser. No. 10/602,930, filed Jun. 24, 2003, and PCT Patent Publication Number WO 2004/002365 are herewith incorporated by reference in their entirety into this specification.

Australian Provisional Application Number PR9617 entitled "Improving Graft Adhesion", and U.S. Patent Application Publication No. US2003-0120332 and PCT Patent Publication Number No. WO03/053287 entitled "Stent Graft With Improved Adhesion" disclose arrangements on stent grafts for enhancing the adhesion of such stent grafts into walls of vessels in which they are deployed. This feature and other features disclosed in Australian Provisional Application Number PR9617, U.S. Patent Application Publication No. US2003-0120332, and PCT Patent Publication Number No. WO03/053287 could be used with the present invention and the disclosure of Australian Provisional Application Number PR9617, U.S. Patent Application Publication No. US2003-0120332, and PCT Patent Publication Number No. WO03/053287 are herewith incorporated by reference in their entirety into this specification.

BRIEF DESCRIPTION OF THE DRAWINGS

This then generally describes the invention but to assist with understanding reference will now be made to the enclosed drawings which show a preferred embodiment of the device and the method of deploying the graft using the device.

In the drawings:

FIG. 3 shows detail of the proximal end of the introducer device according to either FIG. 1 or FIG. 2;

FIG. 4 shows a longitudinal cross-sectional view of the proximal end introducer device shown in FIG. 3 and showing one embodiment of stent graft retained therein;

FIG. 5 shows a transverse cross-sectional view of a side arm of a stent graft suitable for the invention particularly showing a diameter reducing tie arrangement;

DETAILED DESCRIPTION

Figure 1:
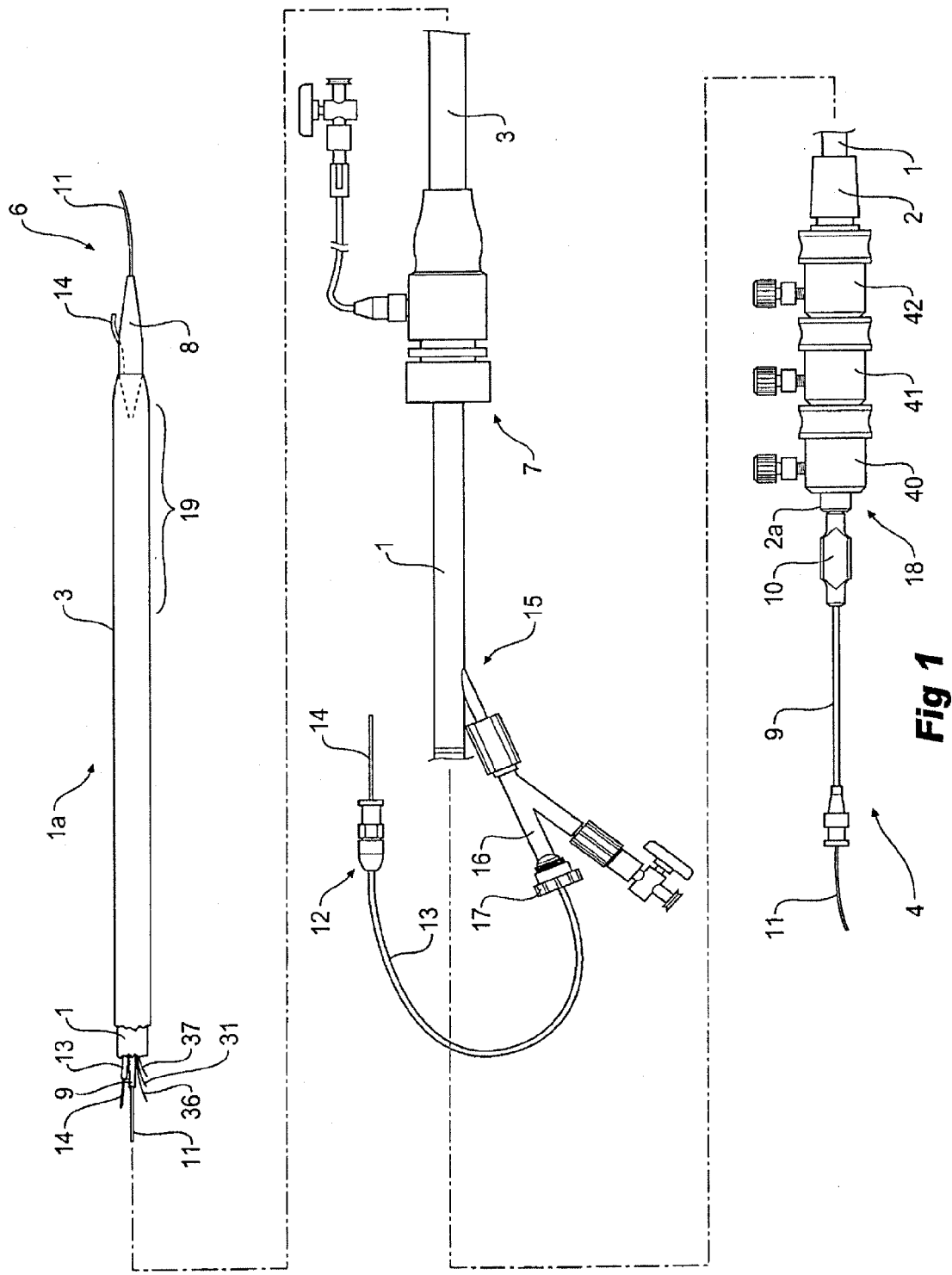
FIG. 1 shows an embodiment of an introducer device according to this invention.

Now looking more closely at the drawings and in particular FIGS. 1 to 5 which show preferred embodiments of deployment devices or introducers according to the invention. In each case the same reference numerals will be used for corresponding components or parts.

It will be seen that the endoluminal deployment device generally comprises an introducer 1a comprising a deployment catheter 1 with a handle 2 at the distal end generally shown as 4. Covering a portion of the deployment catheter 1 is a sheath 3 extending proximally from a sheath manipulator 7.

At the proximal end 6 of the introducer 1a is a nose cone 8. The nose cone is fastened to the guide wire catheter 9 which extends from the distal end 4 of the introducer device to the nose cone. A guide wire 11 extends through the guide wire catheter 9. A pin vice 10 locks the guide wire catheter with respect to the deployment catheter 1 at the distal end 2a of the handle 2.

In the embodiment shown in FIG. 1, proximally of the handle 2 is a "Y" piece 15 in the deployment catheter 1 with a side arm 16 extending from the "Y" piece. Extending through the side arm 16 and through a seal 17 is an auxiliary catheter 13 with an auxiliary guide wire 14 through the auxiliary catheter 13. A grip and syringe adaptor 12 at the distal end of the auxiliary catheter 13 enables connection of a syringe to flush the auxiliary catheter 13 as required.

Figure 2:
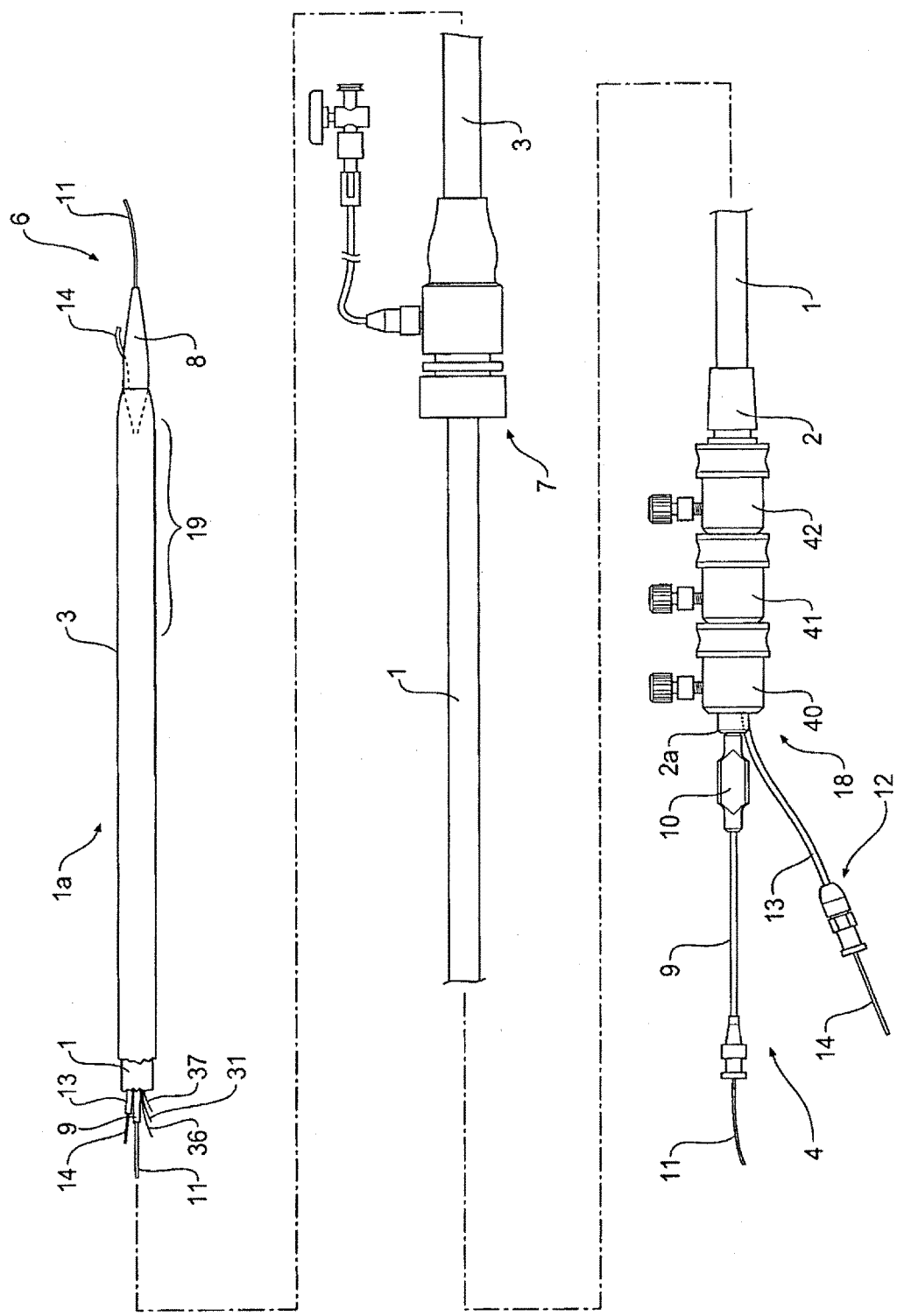
FIG. 2 shows an alternative embodiment of an introducer device according to this invention.

In the embodiment shown in FIG. 2, an auxiliary catheter 13 with an auxiliary guide wire 14 extending through the auxiliary catheter 13 extends from the distal end 2a of the handle 2. A grip and syringe adaptor 12 at the distal end of the auxiliary catheter 13 enables connection of a syringe to flush the auxiliary catheter 13 as required.

On the handle 2 is mounted a set of trigger wire release arrangements generally shown as 18 which will be discussed in detail later.

It will be noted that the nose cone 8 has, as particularly shown in FIG. 4, a longitudinal notch 28 through which passes the auxiliary catheter 13 and auxiliary guide wire 14 so that it extends just beyond the sheath 3. This means that once the introducer has been deployed in substantially the correct position the auxiliary guide wire 14 can be advanced beyond the nose cone 8 so that it can be snared from the side branch artery as will be discussed later.

As can also be seen separately in various embodiments in FIGS. 6 to 10 and in a compressed condition partially in FIG. 3 there is a stent graft 20 which is retained under the sheath 3 in the region 19 on the introducer.

The stent graft 20 has a substantially tubular body with a lumen through it and with a proximal end 21 and a distal end 22. Four different embodiments of stent graft may be applicable to the present invention and these are shown in FIGS. 6 to 9. The embodiment shown in FIG. 9 is partially shown in a compressed condition on the deployment device in FIG. 4. Extending substantially laterally from the tubular body 20 and nearer the proximal end 21 is a side arm 23 again with a lumen through it which is continuous with the lumen of the tubular body 20. As can be particularly seen in FIG. 4 when the stent graft 20 is in a compressed state within the sheath 3, the side arm 23 is directed proximally.

As seen in FIG. 9, the stent graft 20 has zig zag style Gianturco Z stents 24 along its length with a distally extending uncovered zig zag style Gianturco Z stent 26. It should be noted that in some embodiments of the stent graft for placement in the thoracic arch the distally extending uncovered zig zag style Gianturco Z stent 26 may not be present. The side arm 23 also has zig zag Gianturco Z stents 27. The stents are inside the stent graft 20 at the proximal and distal ends and outside the stent graft 20 between the proximal and distal ends. The number of zig zag Gianturco Z stents along the length of the tubular graft 20 will depend upon the length of the stent graft 20.

As can be seen in FIG. 4 and in detail in FIG. 5 the side arm 23 is held in a diameter reduced condition for deployment by means of diameter reducing ties 29. The diameter reducing ties 29 are lengths of suture material which are fastened to the graft material at 30 and are looped around a trigger wire 31 on the opposite side of the side arm and pulled tight so that the diameter of the side arm is reduced. When the trigger wire 31 is released as will be discussed later, the loops of the diameter reducing ties are released and the side arm can expand to its full size. After release the diameter reducing ties remain fixed to the graft material of the side arm.

The auxiliary catheter includes a bulge or "acorn" 44 where it passes through the side arm 23 with extra diameter reducing ties 46 either side of it. These diameter reducing ties 46 effectively grip the auxiliary guide wire catheter either side of the bulge or "acorn". By this arrangement the auxiliary catheter cannot be moved with respect to the side arm unless the diameter reducing ties 46 are removed. This facilitates the moving of the side arm by preventing relative movement of the side arm with respect to the auxiliary catheter 12. The extra diameter reducing ties 46 can be released by the same trigger wire 31 that is used to release the diameter reducing ties 29.

Also on the side arm 23 are radio-opaque markers 33 which enable the position of the side arm to be observed by suitable radio-graphic techniques.

The proximal end 21 of the stent graft 20 is retained in a compressed condition and attached to the guide wire catheter 9 by a release arrangement 35 and a trigger wire 36 to release the release arrangement 35 is also present. Such a retention and release arrangement is depicted in PCT Publication WO 2004/017868 and the disclosure of this patent specification is incorporated by reference in its entirety herein and for all purposes.

A further trigger wire release arrangement (not shown in FIG. 4) is used to retain the distal end of the stent graft at the proximal end of the deployment catheter 1. This distal release arrangement may include a capsule for the exposed stent 26 (see FIG. 9). Such a capsule system is depicted in PCT Publication WO 98/53761 (to which U.S. application Ser. No. 09/449,270 claims priority). The use of a distal capsule system and a deployment system to release an exposed stent is described in U.S. Provisional Patent Application Ser. No. 60/392,667 and the disclosures of those patent specifications are incorporated by reference in their entirety herein and for all purposes.

It will be noted that the auxiliary catheter 13 and the auxiliary guide wire 14 pass through the lumen of the stent graft 20 as well as the lumen of the side arm 23 and then out through the notch 28 in the nose cone 8.

The trigger wire release arrangements 18 on the handle 2 includes three trigger wire release mechanisms. A first trigger wire release mechanism 40 is used to release the distal stent graft release mechanism via trigger wire 37, a second trigger wire release mechanism 41 is used to release the proximal end stent graft release mechanism 35 via trigger wire 36 and the third trigger wire release mechanism 42 is used to pull the trigger wire 31 which releases the diameter reducing ties 29. The trigger wire release mechanisms are operated in the order discussed as will be explained also later with respect to the various stages of deployment according to one embodiment of the invention. In some embodiments of the invention there may be only two trigger wire release mechanisms such as where the proximal and distal ends of the stent graft are retained by the same trigger wire.

Various embodiments of stent graft suitable for use with the present invention will now be discussed with reference to FIGS. 6 to 9. In each case the same reference numerals will be used for corresponding components or parts.

Each of the stent grafts 20 has a tubular body of a biocompatible graft material and zig zag style Gianturco Z stents 24 along its length with a distally extending uncovered zig zag style Gianturco Z stent 26. It should be noted that in some embodiments of the stent graft for placement in the thoracic arch the distally extending uncovered zig zag style Gianturco Z stent 26 may not be present. This may be so, for instance, when the stent graft 20 is a proximal portion of a composite stent grafting system. The use of a composite stent grafting system is described in PCT publication WO 2004/017867, which claims priority to U.S. Provisional Patent Application No. 60/405,769 filed in the United States Patent Office on Aug. 23, 2002, which provisional application became U.S. application Ser. No. 10/645,095 filed in the United States Patent Office on Aug. 21, 2003, and which was published as United States Publication No. US 2004/0082990 which was published on Apr. 29, 2004, the disclosures of this patent specification is incorporated in its entirety herein and for all purposes.

The stents are inside the stent graft 20 at the proximal and distal ends 21, 22 and outside the stent graft 20 between the proximal end 21 and the distal end 22. The number of zig zag Gianturco Z stents along the length of the tubular graft 20 will depend upon the length of the stent graft 20. Normally the zig zag Gianturco Z stents are spaced apart to allow a degree of flexibility of the stent graft so that it can more easily fit the shape of a vessel into which it is deployed.

In each case the stent graft includes a fenestration but the treatment of the fenestration varies.

Figures 6, 7:
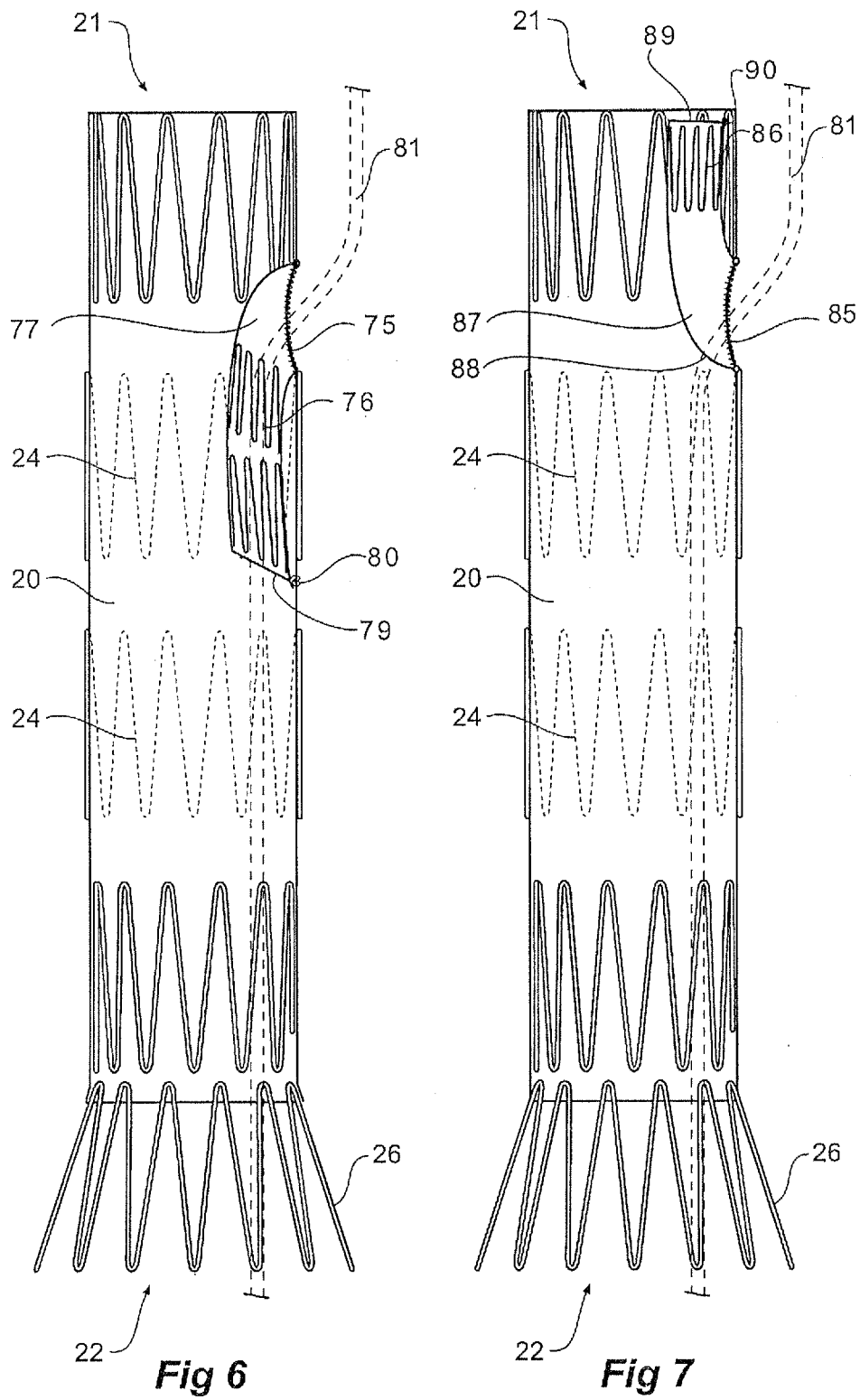
FIG. 6 shows an embodiment of a stent graft suitable for the present invention.
FIG. 7 shows an alternative embodiment of a stent graft suitable for the present invention.

In FIG. 6 the fenestration 75 has a graft material tube 77 fastened around its periphery and extending within the stent graft and towards the distal end 22. The graft material tube 77 includes an external zig zag Gianturco Z stent 76. When a side arm stent graft is deployed through the fenestration 75 into the graft material tube 77 it is into the region of the external zig zag Gianturco Z stent 76 that sealing occurs. The end 79 of the graft material tube 77 is cut off at an angle and fastened by stitching 80 to the stent graft wall 20. The size of the fenestration 75 is preferably somewhat larger than the size of the branch vessel to allow for a degree of misalignment. For instance the fenestration may have an oval shape. The dotted line 81 shows how the auxiliary guide wire catheter passes through the fenestration 75.

In FIG. 7 the fenestration 85 has a graft material tube 87 fastened around its periphery and extending within the stent graft and towards the proximal end 21. The graft material tube 87 includes an external zig zag Gianturco Z stent 86. When a side arm stent graft is deployed through the fenestration 85 into the graft material tube 87 it is into the region of the external zig zag Gianturco Z stent 86 that sealing occurs. The end 89 of the graft material tube 87 is fastened by stitching 90 to the stent graft wall 20. The size of the fenestration 85 is preferably somewhat larger than the size of the branch vessel to allow for a degree of misalignment. For instance the fenestration may have an oval shape. The fenestration 85 may also have a reinforcement ring of Nitinol or similar resilient wire around its periphery. The dotted line 81 shows how the auxiliary guide wire catheter passes through the graft material tube 87 and fenestration 85. At 88 the auxiliary catheter passes through an aperture in the graft material tube 87 which aperture is preferably self sealing so that after removal of the auxiliary guide wire catheter leakage of blood does not occur. This may be achieved by spreading apart the fibres of the graft material tube to allow the auxiliary catheter to pass through rather than cutting them at 88. Alternatively some form of flap valve may be used.

In an alternative arrangement the auxiliary catheter may have a zig zag configuration and pass up through the stent graft 20 and enter the graft material tube 87 at its end 89 and then exit through the fenestration 85.

Figure 8:
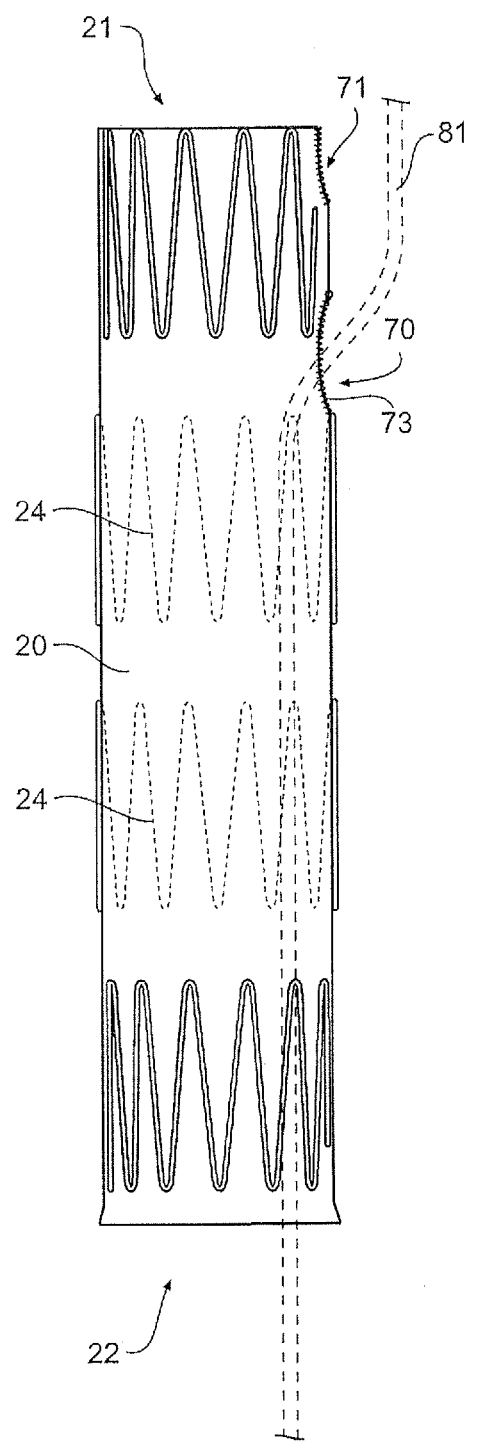
FIG. 8 shows an alternative embodiment of a stent graft suitable for the present invention.
Figure 9:
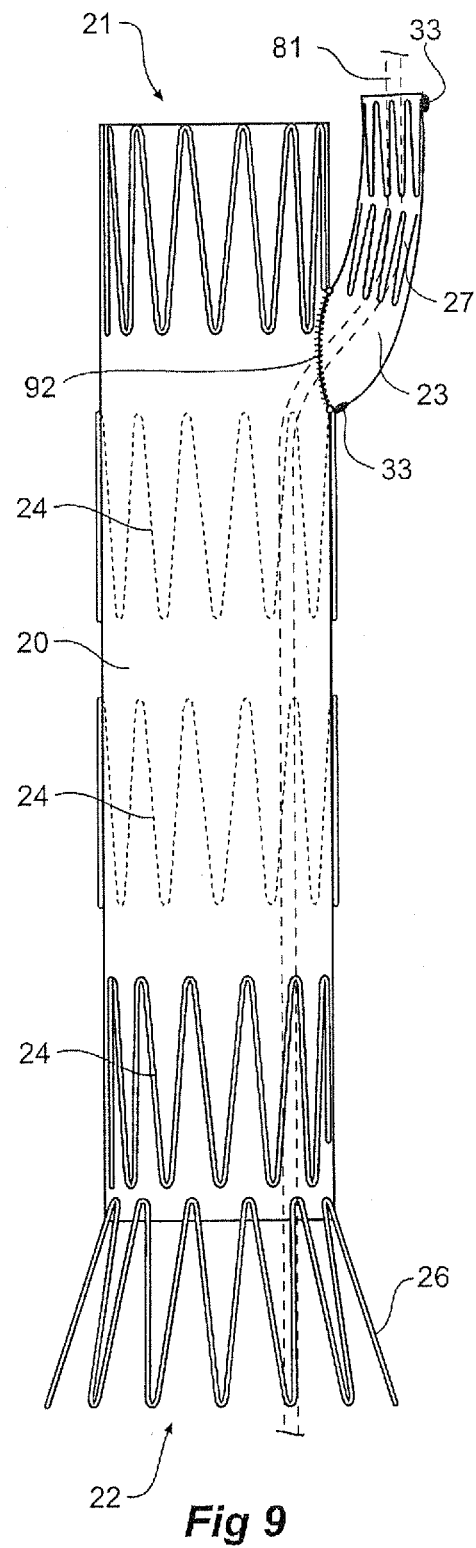
FIG. 9 shows an alternative embodiment of a stent graft suitable for the present invention.

In FIG. 8 the stent graft 20 merely has a fenestration 70 with a reinforcement ring 73 of Nitinol or similar resilient wire around its periphery. When a side arm stent graft is deployed through the fenestration into the stent graft 20 sealing occurs around the periphery of the fenestration. The size of the fenestration 70 is preferably slightly smaller than the size of the side arm stent graft to be placed into the branch vessel to allow for sealing. In this embodiment stent graft 20 includes a scalloped end 71 to allow the stent graft to be placed over the adjacent carotid artery. Such a scalloped end may also be used with the other embodiments of stent graft. The dotted line 81 shows how the auxiliary guide wire catheter passes through the lumen of the stent graft 20 and fenestration 75.

In FIG. 9 the fenestration 92 has a graft material tube 23 fastened around its periphery and extending from the stent graft. The fenestration 92 may also have a reinforcement ring of Nitinol or similar resilient wire around its periphery. The graft material tube 23 includes one or more external zig zag Gianturco Z stents 27. The dotted line 81 shows how the auxiliary guide wire catheter passes through the graft material tube 23 and fenestration 92. The side arm 23 includes radio-opaque markers 33 to assist with placement.

The various stages of deployment of one embodiment of the stent graft 20 into the thoracic arch of a patient will now be discussed with reference to FIGS. 10 to 17. The deployment device can be the type shown in either FIG. 1 or FIG. 2.

The thoracic arch region of a patient generally comprises an ascending aorta 50 extending from an aortic valve 51 of the heart of the patient, then over the thoracic arch 52 to the descending aorta 53. From the thoracic arch three main arteries extend. These are the innominate artery 54, the left carotid artery 55 and a subclavian artery 56. This embodiment of the invention will generally be discussed with reference to deployment of a stent graft with a side branch into the aorta and left subclavian artery but the invention is not so restricted.

A stent graft may be necessary in the aortic arch region when an aneurysm 57 in the aorta extends up the aorta to such an extent that there is insufficient patent aortic wall to provide good sealing for a stent graft distally of the left subclavian artery 56. It is desirable in such circumstances to extend the stent graft to seal onto good artery wall at least between the left carotid artery 55 and the left subclavian artery 56.

The invention is not limited to this particular application but will be discussed in relation to this particular application.

Figure 10:
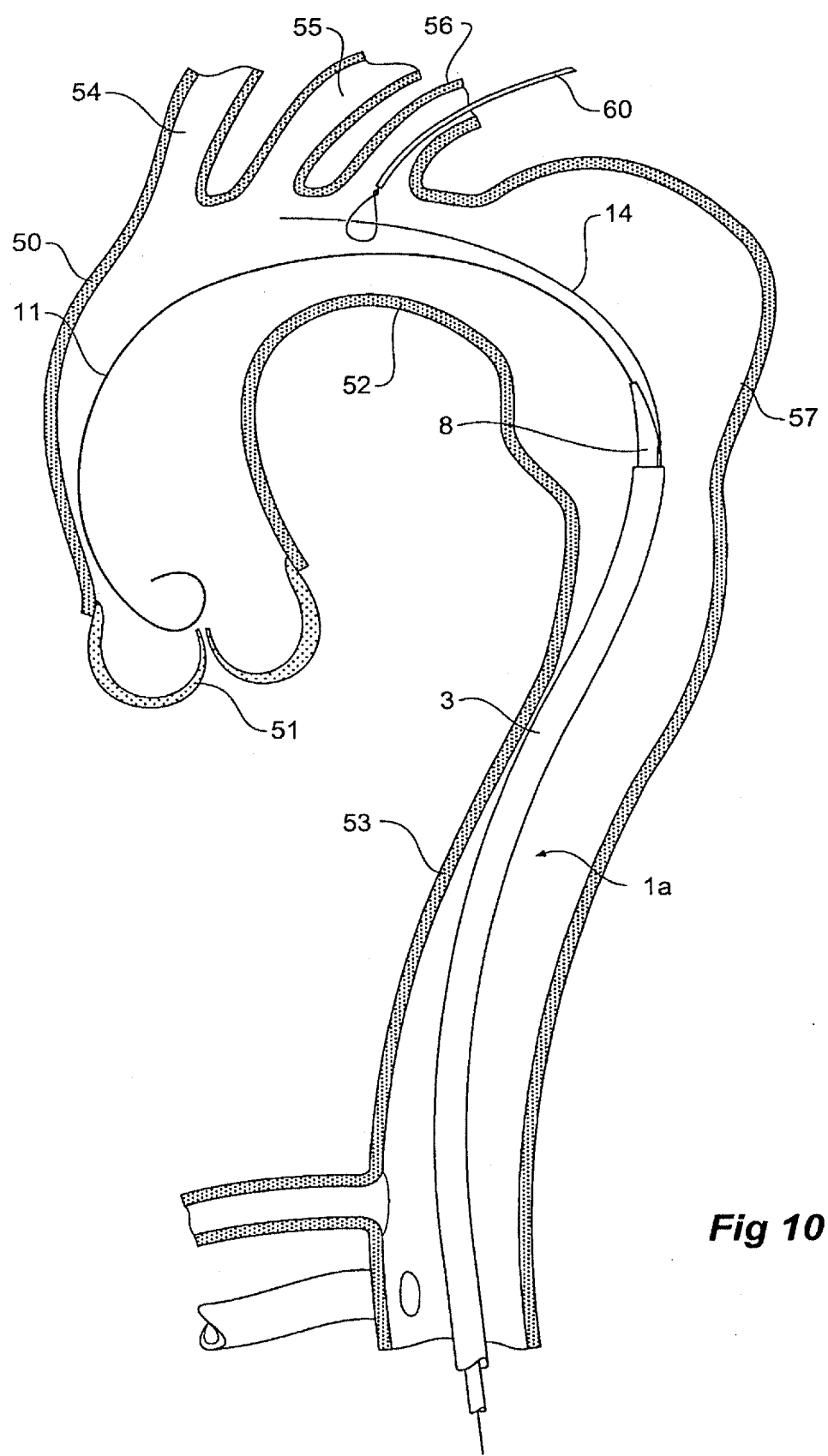
FIG. 10 shows a schematic view of the first stage of deployment of the introducer device shown in FIG. 1 or FIG. 2 and including a stent graft as shown in FIG. 9 into a thoracic arch of a patient.

As can be seen in FIG. 10 the introducer 1a has been introduced into the aorta normally via an incision into the femoral artery over a guide wire 11. The guide wire 11 has been deployed down towards the aortic valve 51. Once the introducer is in position the auxiliary guide wire 14 is extended beyond the nose cone 8 of the introducer until it is adjacent the left subclavian artery. A suitable radio-graphic tip may be provided on the guide wire to assist with determination of its location.

An incision can then be made into the brachial artery of the left arm and a snare catheter 60 introduced into the brachial artery and via that to the left subclavian artery and this snare catheter has a loop 61 at its end which can then be used to snare the guide wire 14. The snare is used to grip and pull the flexible guide wire 14 into the left subclavian artery and out through the brachial artery.

Figure 11:
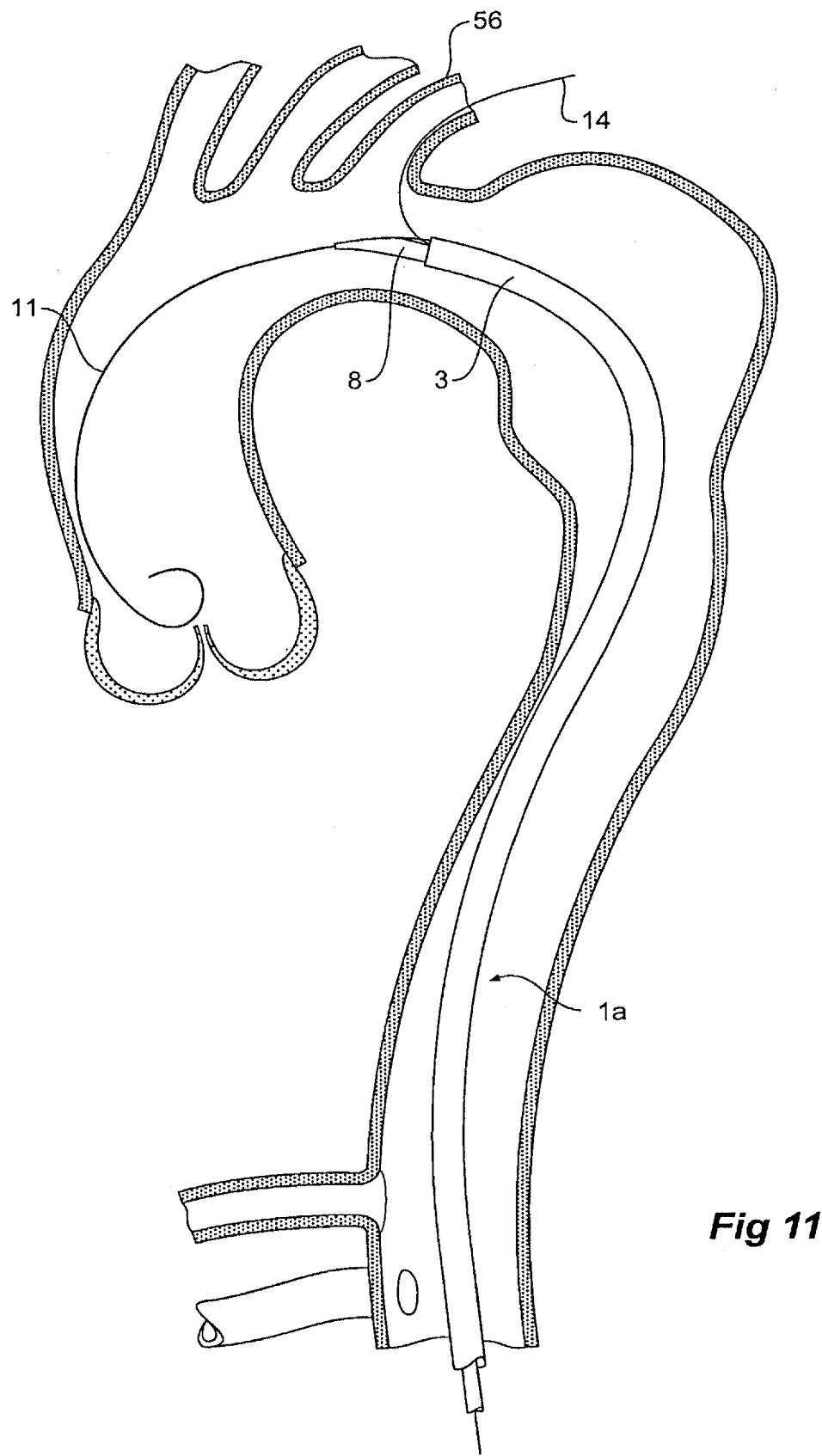
FIG. 11 shows a second stage in the process with the auxiliary guide wire snared.

In the next stage shown in FIG. 11 the introducer 1a is advanced proximally over the guide wire 11 with the auxiliary guide wire 14 still extending into the left subclavian artery. The introducer is advanced until the nose cone is adjacent the left subclavian artery and the sheath 3 is just distal of the opening of the artery into the thoracic arch.

Figure 12:
FIG. 12 shows a further stage with a protective catheter passed over auxiliary guide wire.

As can be seen in FIG. 12 a protective catheter or sleeve 62 is deployed onto the auxiliary guide wire where it exits from the brachial artery and is then slid over the auxiliary guide wire 14 from the brachial artery end to protect the junction 57 of the left subclavian artery with the thoracic arch during the subsequent steps. The protective catheter or sleeve 62 and the auxiliary guide wire 14 are then locked together so that they can be used to pull the side arm 23 of the stent graft into the left subclavian artery 56.

Figure 13:
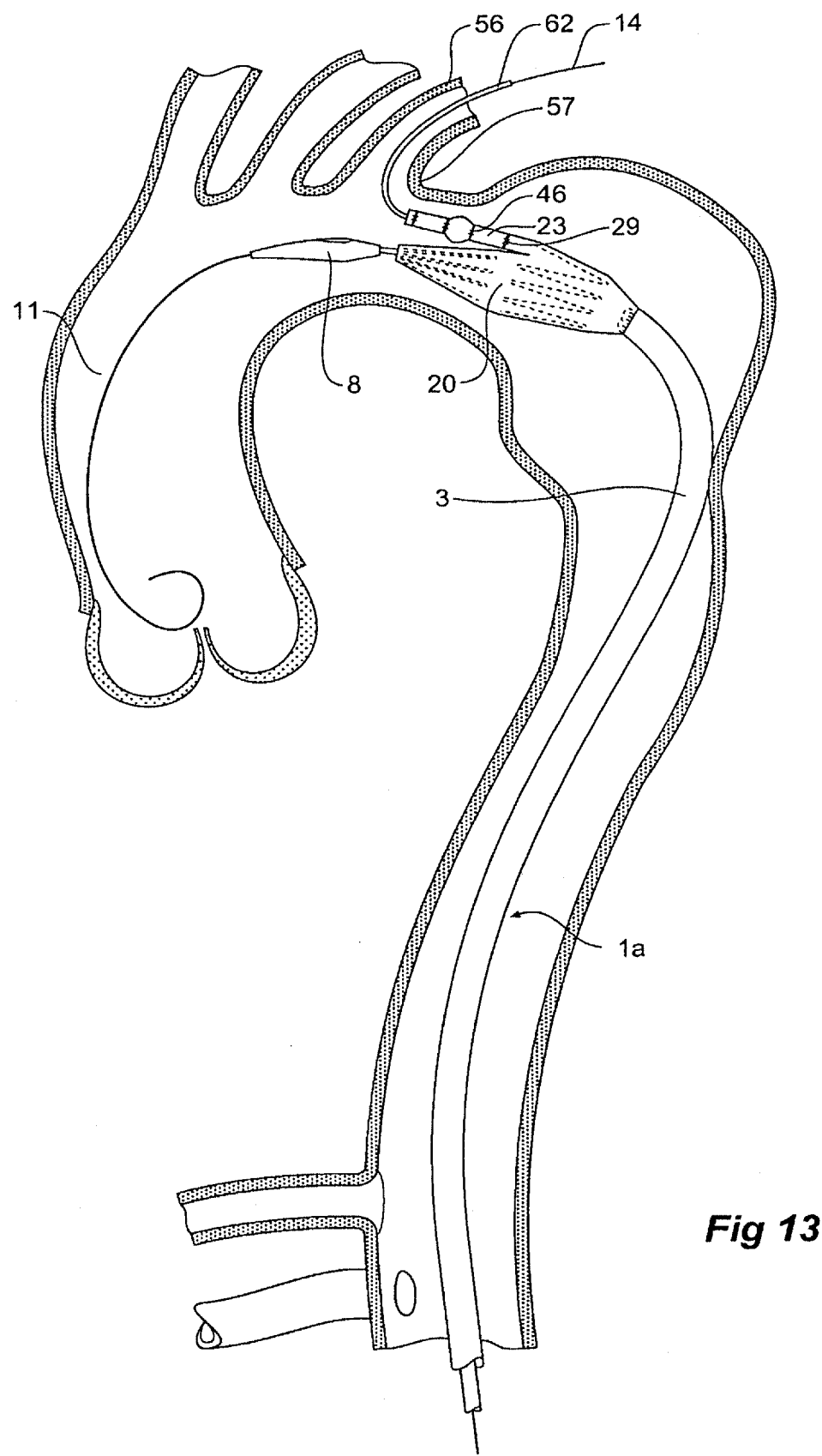
FIG. 13 shows a further stage with the sheath on the deployment device withdrawn partially.

As can be seen in FIG. 13 the sheath 3 of the introducer 1a has been partially withdrawn so that the stent graft 20 retained by the sheath 3 has expanded but the retention arrangement 35 still holds the proximal end 21 of the graft in a restrained condition. The side arm 23 is also released from the sheath but still held in a retracted condition by diameter reducing ties 29. It will be noted that at this stage the distal end 22 of the stent graft is still retained within the sheath 3.

Figure 14:
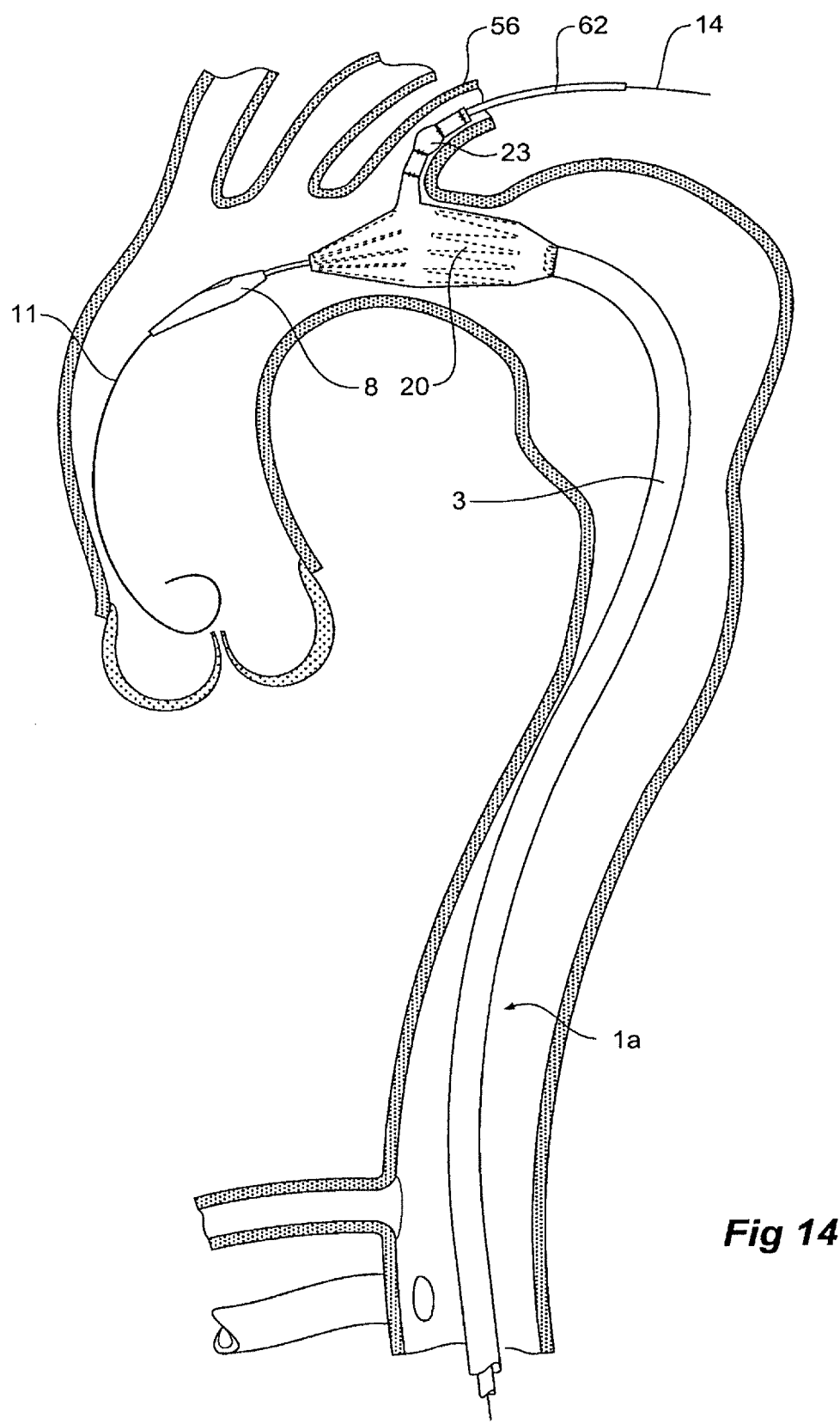
FIG. 14 shows the next stage of deployment with the side arm drawn into the subclavian artery.

As shown in FIG. 14, the introducer 1a is then moved further proximally while pulling on the protection catheter 62 and guide wire 14 so that the side arm 23 of the stent graft 20 is pulled into the left subclavian artery 56.

Figure 15:
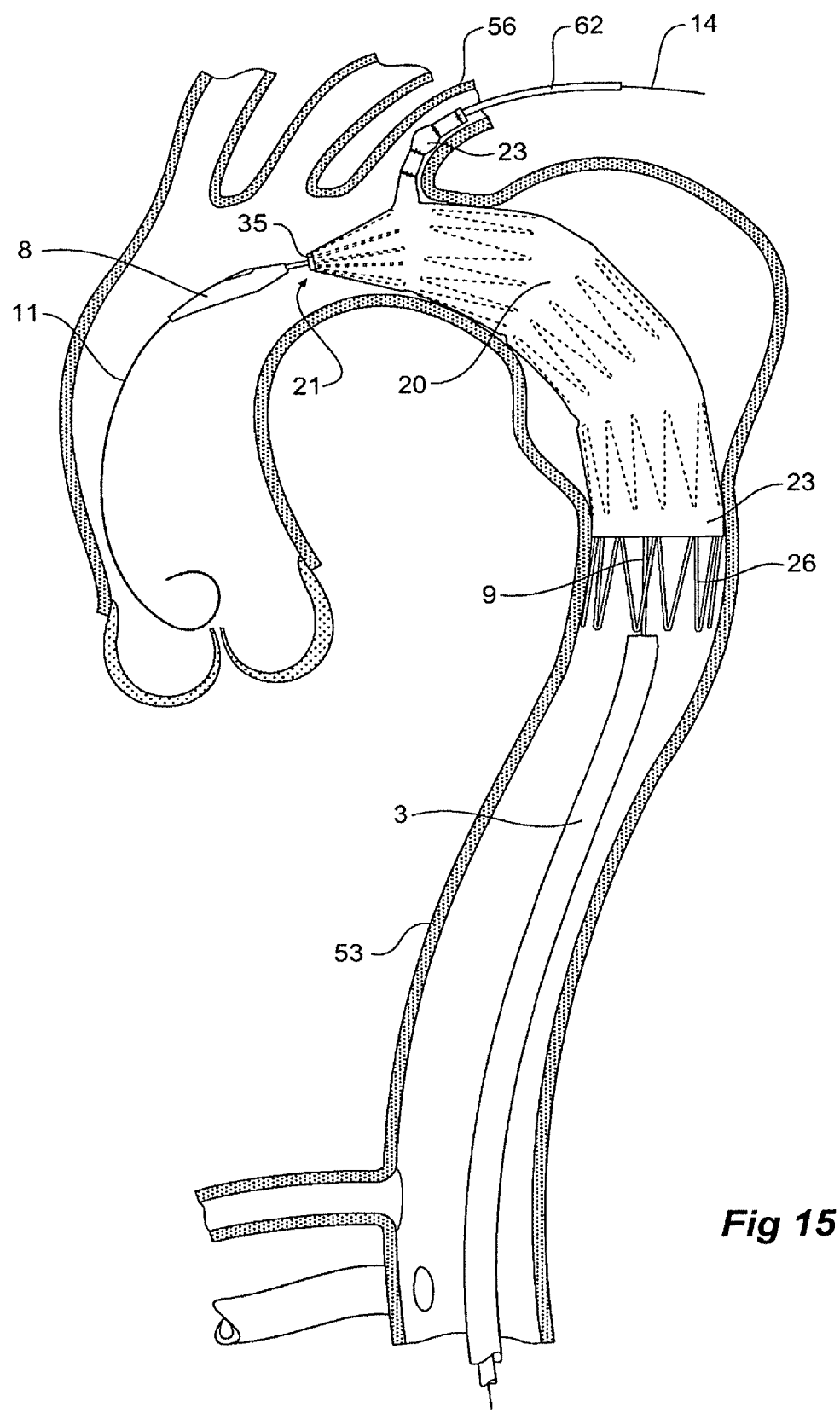
FIG. 15 shows the first stage of release of the stent graft from the introducer device.

As shown in FIG. 15 the sheath 3 is then pulled further back so that the distal end of the graft 20 is released from the sheath 3 and then the distal trigger wire release mechanism 40 (see FIG. 1) can be released to release the external zig zag stents 26 so that they expand against the wall of the descending aorta 53.

Figure 16:
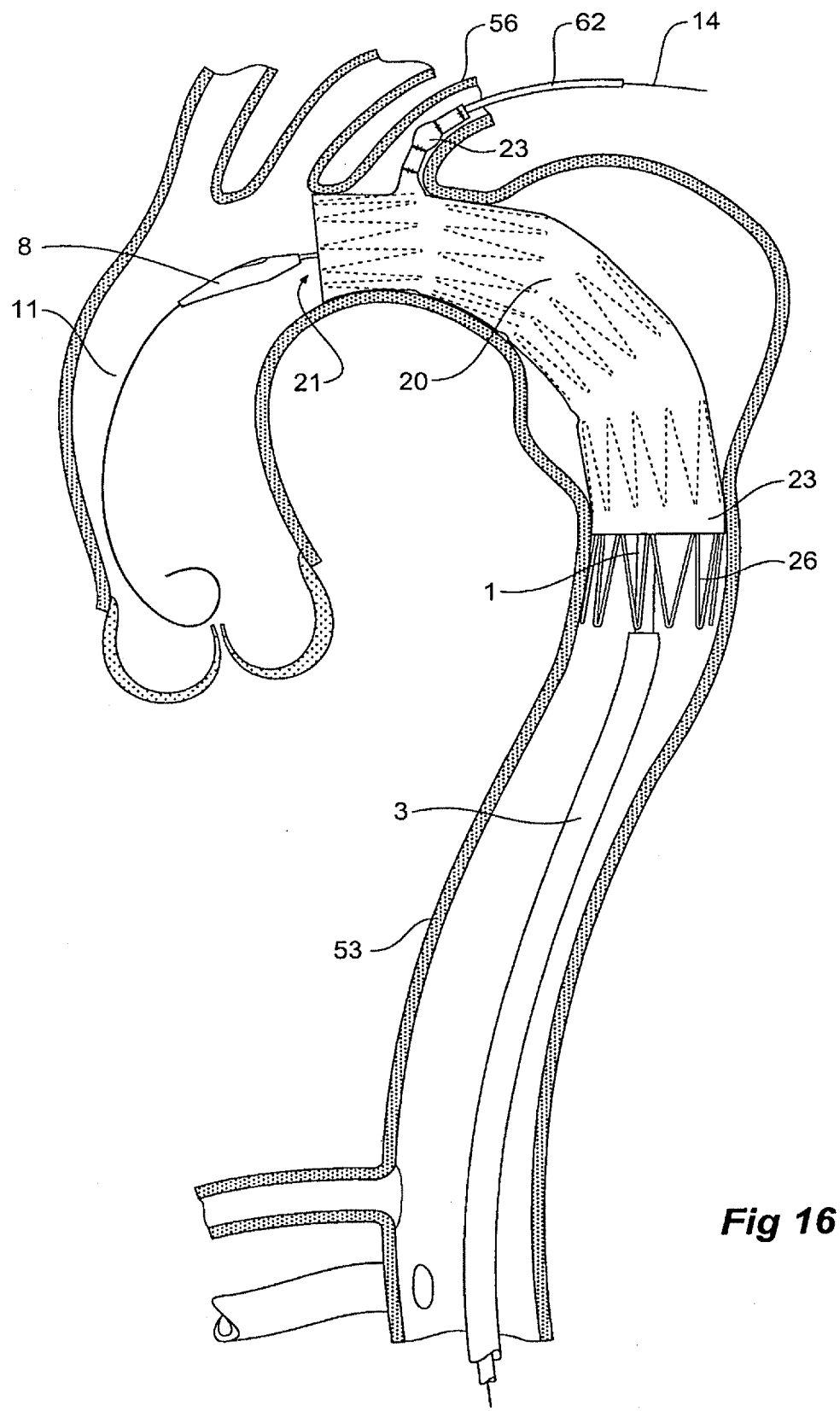
FIG. 16 shows the second stage of release of the stent graft from the introducer device.

Next as shown in FIG. 16 the proximal end 21 of the graft 20 is released by releasing the retention mechanism 35 (see FIG. 1) by pulling on the trigger wire release mechanism 41 which pulls out trigger wire 36.

Figure 17:
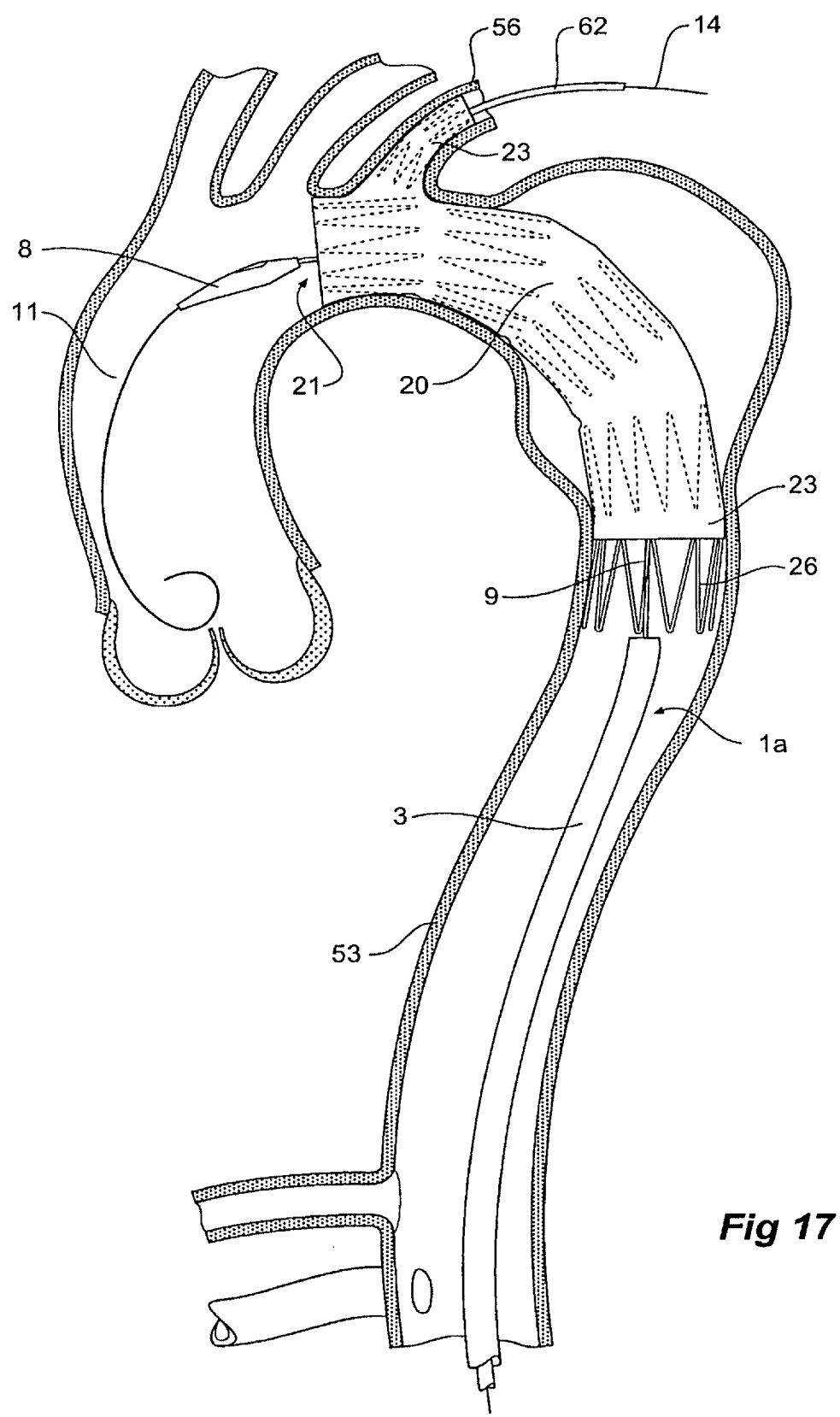
FIG. 17 shows the final stage of release of the stent graft from the introducer.

Finally as shown in FIG. 17 the diameter reducing ties are released by pulling on the trigger wire release mechanism 42 (see FIG. 1) which pulls the trigger wire 31.

The auxiliary guide wire 14 can then be retracted into the introducer 1a and the introducer removed from the aorta to leave the stent graft 20 deployed in the aorta with the side arm 23 deployed into the left subclavian artery 56.

Figure 18:
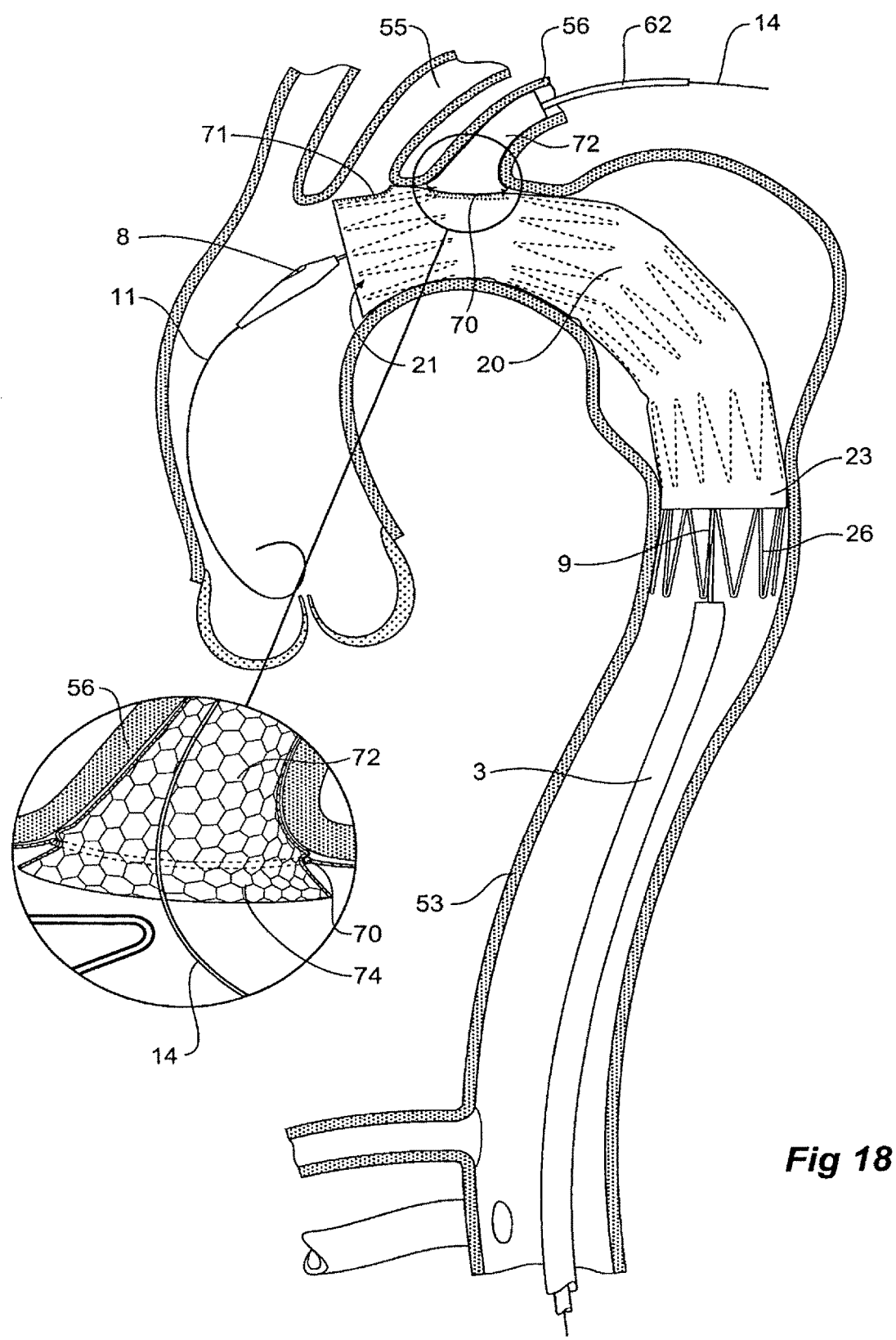
FIG. 18 shows a schematic and detailed view of the deployment of a stent graft of a type as shown in FIG. 8 into a thoracic arch of a patient.

FIG. 18 shows a schematic and a detailed view of the deployment of a stent graft as shown in FIG. 8 into a thoracic arch of a patient. After the introducer is deployed into the thoracic arch and the auxiliary guide wire snared as shown in FIGS. 10 and 11 the introducer is further advanced proximally over the main guide wire 11 until the fenestration 70 (see also FIG. 8) is adjacent the subclavian artery 56. It will be noted that at this stage the scallop 71 at the distal end 21 of the stent graft 20 is positioned around the adjacent carotid artery 55 so as not to occlude it. This arrangement enables the distal end 21 of the stent graft 20 to have a larger landing zone in the thoracic arch while not occluding the carotid artery. A separate balloon expandable stent graft 72 can then be deployed brachially and through the subclavian artery over the auxiliary guide wire 14 so that its proximal end 74 enters the fenestration 70 and then it can be balloon expanded so that the end 74 is in effect crimped around the fenestration 70 to securely retain the stent graft 72 in the fenestration 70.

Figure 19:
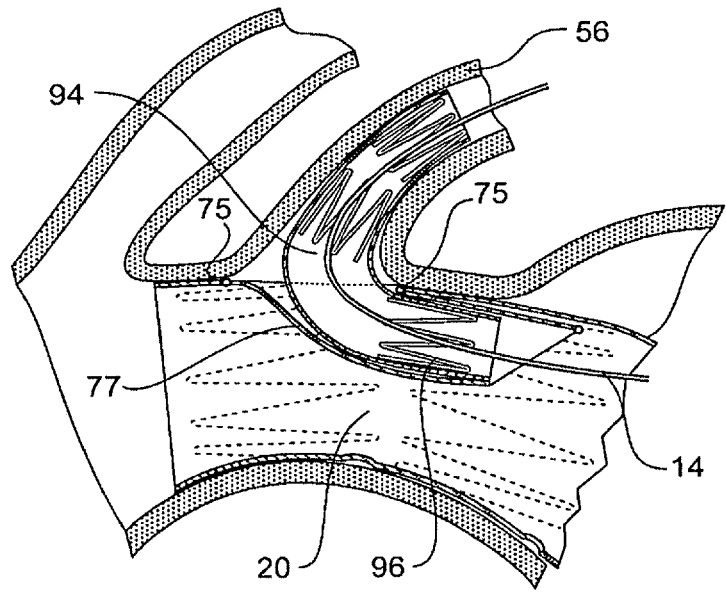
FIG. 19 shows a detailed view of the deployment of a stent graft of a type as shown in FIG. 6 into a thoracic arch of a patient.

FIG. 19 shows a detailed view of the deployment of a stent graft as shown in FIG. 6 into a thoracic arch of a patient. After the introducer is deployed into the thoracic arch and the auxiliary guide wire snared as shown in FIGS. 10 and 11 the introducer is further advanced proximally over the main guide wire 11 (see FIG. 11) until the fenestration 75 (see also FIG. 6) is adjacent the subclavian artery 56. A separate balloon expandable or self expanding stent graft 94 can then be deployed brachially through the subclavian artery over the auxiliary guide wire 14 so that its proximal end 96 enters the fenestration 75 and then it can be allowed to expand or be balloon expanded so that the end is expanded within the graft material tube 77 to seal the side arm stent graft 94 into the main stent graft 20.

Figure 20:
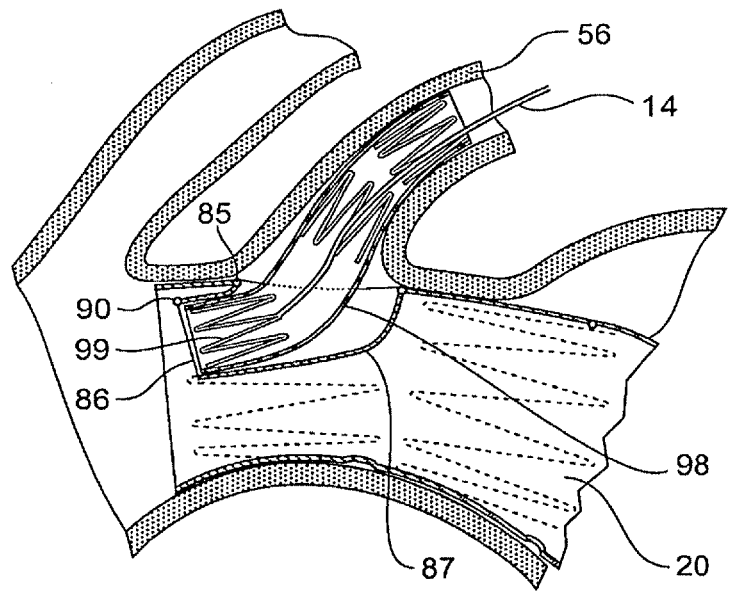
FIG. 20 shows a detailed view of the deployment of a stent graft of a type as shown in FIG. 7 into a thoracic arch of a patient.

FIG. 20 shows a detail view of the deployment of a stent graft as shown in FIG. 7 into a thoracic arch of a patient. After the introducer is deployed into the thoracic arch and the auxiliary guide wire snared as shown in FIGS. 10 and 11 the introducer is further advanced proximally over the main guide wire 11 until the fenestration 85 (see also FIG. 7) is adjacent the subclavian artery 56. A separate balloon expandable or self expanding stent graft 98 can then be deployed brachially through the subclavian artery over the auxiliary guide wire 14 so that its proximal end 99 enters the fenestration 75 and then it can be allowed to expand or be balloon expanded so that the end is expanded within the graft material tube 87 to seal the side arm stent graft 98 into the main stent graft 20.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A deployment system for deploying a self-expanding fenestrated stent graft comprising:
an introducer having a proximal end intended to be employed in a patient during use and a distal end intended to remain outside of the patient during use, a nose cone at the proximal end of the introducer;
a stent graft retained on the introducer and having a main graft body, a proximal fluid inflow end, a distal fluid outflow end, a lumen from the proximal fluid inflow end to the distal fluid outflow end, a graft wall, at least one self-expanding stent supporting the main graft body, a fenestration in the graft wall having a periphery, and an internal branch extending from the fenestration and into the lumen of the stent graft, the internal branch having a first end attached to the graft wall at the fenestration, a second end extending toward the stent graft proximal fluid inflow end and fixedly fastened to the graft wall inside the stent graft, and a branch lumen therethrough;
a main catheter disposed in the introducer and extending from the distal end of the introducer to the proximal end of the introducer, the main catheter having a main catheter lumen configured to slidably receive a guide wire in the main catheter lumen; and
an auxiliary catheter preloaded within the introducer prior to delivery to a patient at least partially adjacent the main catheter, the auxiliary catheter including an auxiliary lumen configured to receive an auxiliary guide wire slideably disposed in the auxiliary lumen, the auxiliary catheter extending from a distal position to the distal fluid outflow end of the stent graft, into the lumen of the stent graft, into the lumen of the internal branch, and through the fenestration, wherein the auxiliary catheter is preloaded at least partially within the lumen of the stent graft, within the lumen of the internal branch and extends out of the fenestration and to the nose cone.

2. A deployment system of claim 1, wherein the at least one self-expanding stent comprises a stent framework supporting the graft body substantially along its length.

3. The deployment system of claim 1, wherein the internal branch comprises a graft material tube that is at least partially unstented.

4. The deployment system of claim 1, wherein the second end of the internal branch is secured to an internal surface of the graft wall.

5. The deployment system of claim 1, wherein the fenestration periphery has a reinforcement about the fenestration periphery.

6. The deployment system of claim 1, wherein the internal branch is parallel to the graft wall and the second end of the internal branch extends towards the proximal fluid inflow end of the stent graft and is configured to provide antegrade flow through the internal branch lumen.

7. The deployment system of claim 1, wherein the nose cone includes a notch in an exterior surface of the nose cone and wherein the preloaded auxiliary catheter extends out of the fenestration, to the nose cone, and at least partially resides in the notch.

8. The deployment system of claim 1, wherein the internal branch comprises a graft material tube having a side wall and the auxiliary catheter passes through an aperture in the side wall of the graft material tube from the lumen of the stent graft and into the lumen of the internal branch.

9. The deployment system of claim 8, wherein the auxiliary catheter passes through a self-sealing aperture in the wall of the graft material tube.

10. The deployment system of claim 1, wherein the internal branch is disposed within the lumen of the stent graft in a pre-deployment condition and a post-deployment condition.

11. A deployment system for deploying a self-expanding fenestrated stent graft comprising:
an introducer having a proximal end intended to be employed in a patient during use and a distal end intended to remain outside of the patient during use, a nose cone at the proximal end of the introducer;
a stent graft retained on the introducer and having a main graft body, a proximal end, a distal end, a lumen from the proximal end to the distal end, a graft wall, at least one self-expanding stent supporting the main graft body, a fenestration in the graft wall having a periphery, and an internal branch extending from the fenestration and into the lumen of the stent graft, the internal branch having a first end attached to the graft wall at the fenestration, a second end extending toward the proximal end of the stent graft and fixedly fastened to the graft wall inside the stent graft, and a branch lumen therethrough;

a main catheter disposed in the introducer and extending from the distal end of the introducer to the proximal end of the introducer, the main catheter having a main catheter lumen configured to slidably receive a guide wire in the main catheter lumen; and an auxiliary catheter preloaded within the introducer prior to delivery to a patient at least partially adjacent the main catheter, the auxiliary catheter including an auxiliary lumen configured to receive an auxiliary guide wire slideably disposed in the auxiliary lumen, the auxiliary catheter extending from a distal position to the distal end of the stent graft, into the lumen of the stent graft, into the lumen of the internal branch, and through the fenestration, wherein the auxiliary catheter is preloaded at least partially within the lumen of the stent graft, within the lumen of the internal branch and extends out of the fenestration and to the nose cone; wherein the nose cone includes a notch in an exterior surface of the nose cone and wherein the preloaded auxiliary catheter extends out of the fenestration, to the nose cone, and at least partially resides in the notch.

12. The deployment system of claim 1, wherein the internal branch comprises a graft material tube and the auxiliary catheter penetrates the graft material of the graft material tube and into the lumen of the internal branch.

13. A deployment system for deploying a self-expanding fenestrated stent graft comprising:

an introducer having a proximal end intended to be employed in a patient during use and a distal end intended to remain outside of the patient during use, a nose cone at the proximal end of the introducer;

a stent graft retained on the introducer and having a main graft body, a proximal inflow end, a distal outflow end, a lumen from the proximal inflow end to the distal outflow end, a graft wall, at least one self-expanding stent supporting the main graft body, a fenestration in the graft wall having a periphery, and an internal branch extending from the fenestration and into the lumen of the stent graft, the internal branch having a first end attached to the graft wall at the fenestration, a second end extending toward the proximal inflow end and fixedly fastened to the graft wall inside the graft, and a branch lumen therethrough;

a main catheter disposed in the introducer and extending from the distal end of the introducer to the proximal end of the introducer, the main catheter having a main catheter lumen configured to slidably receive a guide wire in the main catheter lumen; and an auxiliary catheter preloaded within the introducer prior to delivery to a patient at least partially adjacent the main catheter, the auxiliary catheter including an auxiliary lumen configured to receive an auxiliary guide wire slideably disposed in the auxiliary lumen, the auxiliary catheter extending from a distal position to the distal end of the stent graft, into the lumen of the stent graft, into the lumen of the internal branch, and through the fenestration, wherein the auxiliary catheter is preloaded at least partially within the lumen of the stent graft, within the lumen of the internal branch and extends out of the fenestration and to the nose cone; wherein the auxiliary catheter passes through a self-sealing aperture in a wall of a graft material tube of the internal branch.

14. A device deployment system for deploying a self-expanding branched stent graft comprising:

an introducer having a proximal end intended to be employed in a patient during use and a distal end intended to remain outside of the patient during use;

a stent graft retained on the introducer comprising a proximal fluid inflow end, a distal fluid ouflow end, a stent graft lumen from the proximal fluid inflow end to the distal fluid outflow end, a graft wall, and a self-expanding stent framework supporting the stent graft, a fenestration in the graft wall, and an internal branch extending from the fenestration and into the lumen of the stent graft, the internal branch having a first end attached to the graft wall at the fenestration, a second end having an opening extending toward the proximal fluid inflow end of the stent graft and fixedly fastened to the graft wall inside the stent graft, and a branch lumen therethrough;

a main catheter disposed in a lumen of the introducer and the stent graft lumen and extending from the distal end to the proximal end of the introducer, the main catheter having a lumen configured to slidably receive a guide wire in the main catheter lumen; and an auxiliary catheter disposed at least partially adjacent the main catheter in the stent graft lumen, the auxiliary catheter including an auxiliary lumen configured to slidably receive an auxiliary guide wire in the auxiliary lumen, the auxiliary catheter extending from a distal position to the distal fluid outflow end of the stent graft, into the lumen of the stent graft, through a wall of the internal branch, through the lumen of the internal branch, and out of the fenestration, wherein the auxiliary catheter is preloaded at least partially within the lumen of the stent graft, within the lumen of the internal branch and extends out of the fenestration.

15. The deployment system of claim 14, wherein the introducer further includes a nose cone at the proximal end of the introducer.

16. The deployment system of claim 15, wherein the nose cone comprises a longitudinal notch and a portion of the auxiliary catheter is disposed in the longitudinal notch.

17. The deployment system of claim 14, wherein the internal branch is disposed within the lumen of the stent graft in a pre-deployment condition and a post-deployment condition.

18. A deployment system for deploying a composite stent graft comprising:

a first introducer having a proximal end intended to be employed in a patient during use and a distal end intended to remain outside of the patient during use, a nose cone at the proximal end of the first introducer;

a first stent graft retained on the first introducer and having a main graft body, a proximal fluid inflow end, a distal fluid outflow end, a lumen from the proximal fluid inflow end to the distal fluid outflow end, a graft wall, at least one self-expanding stent supporting the main graft body, a fenestration in the graft wall having a periphery, and an internal branch extending from the fenestration and into the lumen of the main graft body, the internal branch having a first end attached to the graft wall at the fenestration, a second end extending toward the first stent graft proximal fluid inflow end and fixedly fastened to the graft wall inside the first stent graft, and a branch lumen therethrough;

a second stent graft, wherein the first stent graft is a proximal portion of the composite stent graft and the distal fluid outflow end of the first stent graft is configured to be connected to the second stent graft;

a main catheter disposed in the first introducer and extending from the distal end of the first introducer to the proximal end of the first introducer, the main catheter having a lumen configured to slidably receive a guide wire in the main catheter lumen; and an auxiliary catheter preloaded within the first introducer prior to delivery to a patient at least partially adjacent the main catheter, the auxiliary catheter including an auxiliary lumen configured to receive an auxiliary guide wire slideably disposed in the auxiliary lumen, the auxiliary catheter extending from a distal position to the distal fluid outflow end of the first stent graft, into the lumen of the first stent graft, into the lumen of the internal branch, and through the fenestration, wherein the auxiliary catheter is preloaded at least partially within the lumen of the first stent graft, within the lumen of the internal branch and extends out of the fenestration.

19. The deployment system of claim 18, wherein the internal branch is disposed within the lumen of the first stent graft in a pre-deployment condition and a post-deployment condition.

\* \* \* \* \*